(12) United States Patent
Ziyatdinov

(10) Patent No.: US 11,390,896 B2
(45) Date of Patent: Jul. 19, 2022

(54) **METHOD FOR PRODUCING L-METHIONINE USING A BACTERIUM OF THE GENUS *PANTOEA***

(71) Applicant: AJINOMOTO CO., INC., Tokyo (JP)

(72) Inventor: Mikhail Kharisovich Ziyatdinov, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 17/081,626

(22) Filed: Oct. 27, 2020

(65) Prior Publication Data

US 2021/0054425 A1 Feb. 25, 2021

Related U.S. Application Data

(63) Continuation of application No. PCT/JP2019/018057, filed on Apr. 26, 2019.

(30) Foreign Application Priority Data

May 4, 2018 (RU) ................................ 2018116608

(51) Int. Cl.
*C12P 13/12* (2006.01)

(52) U.S. Cl.
CPC .................................. *C12P 13/12* (2013.01)

(58) Field of Classification Search
CPC ........................................................ C12P 13/12
See application file for complete search history.

(56) References Cited

U.S. PATENT DOCUMENTS

| | | |
|---|---|---|
| 4,278,765 A | 7/1981 | Debabov et al. |
| 4,346,170 A | 8/1982 | Sano et al. |
| 5,661,012 A | 8/1997 | Sano et al. |
| 5,965,391 A | 10/1999 | Reinscheid et al. |
| 6,040,160 A | 3/2000 | Kojima et al. |
| 7,611,873 B1 | 11/2009 | Usuda et al. |
| 7,790,424 B2 | 9/2010 | Park et al. |
| 2006/0216796 A1 | 9/2006 | Hashiguchi et al. |
| 2012/0015409 A1 | 1/2012 | Tabata et al. |

FOREIGN PATENT DOCUMENTS

| | | |
|---|---|---|
| EP | 0685555 A1 | 12/1995 |
| EP | 2345667 A2 | 7/2011 |
| EP | 2395096 A1 | 12/2011 |
| EP | 2861726 B1 | 5/2017 |
| EP | 2633037 B1 | 6/2017 |
| WO | WO95/16042 A1 | 6/1995 |
| WO | WO96/15246 A1 | 5/1996 |
| WO | WO02/10209 A1 | 2/2002 |
| WO | WO2017/146195 A1 | 8/2017 |

OTHER PUBLICATIONS

Sousa et al., Microbiology 148(Pt5): 1291-1303, 2002.*
Witkowski et al., Biochemistry 38:11643-11650, 1999.*
Tang et al., Phil Trans R Soc B 368:20120318, 1-10, 2013.*
Seffemick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Zhou et al., Cell Mol Life Sci 63(19-20):2260-2290, 2006.*
Kozak, M., Gene 234:187-208, 1999.*
GenBank WP_014595016, Oct. 5, 2017.*
De Maayer et al., GenBank accession No. ADD75339, Jan. 30, 2014.*
EcoCyc database, https://ecocyc.org/, accession ID: EG11466, 2006, pp. 1-4; retrieved Oct. 21, 2020.
International Search Report and Written Opinion for International App No. PCT/JP2019/018057 dated Aug. 14, 2019.
Saier, Jr., M. H., et al., "The Transporter Classification Database (TCDB): recent advances," Nucleic Acids Research 2016;44:D372-D379.

* cited by examiner

*Primary Examiner* — Delia M Ramirez
(74) *Attorney, Agent, or Firm* — Cermak Nakajima & McGowan LLP; Shelly Guest Cermak

(57) ABSTRACT

The present invention provides a method for producing L-methionine by fermentation using a bacterium belonging to the genus *Pantoea* which has been modified to overexpress the rarD gene or a mutant gene thereof.

7 Claims, No Drawings

Specification includes a Sequence Listing.

SEQUENCE LISTING

<160> NUMBER OF SEQ ID NOS: 16

<210> SEQ ID NO 1
<211> LENGTH: 900
<212> TYPE: DNA
<213> ORGANISM: Pantoea ananatis

<400> SEQUENCE: 1

```
atggatccc agcaaaccg tcagggcatc ggctttgcgc ttggcgctta ctttatttgg      60
ggcattgcgc ccgcctactt caaattagtg aaggccgtac cggcgactga aatcatgacc     120
cacagggtga tctggtcagc actgttcatg ttgttactga ttaccctgag tcgcagttgg     180
ggacaggtca gaagcgtgct gcgccagcca aaaaaagtgc tgctactggc ccttacggcg     240
gtaacggtag ggggaaactg gttgctgttt atctgggcgg tgaacaatca gcatatgctt     300
gaagccagcc tgggctattt tatcaacccg ttgattaacg ttgtgtttgg catgattttc     360
ctgcgtgaac gtttccgtcg cctgcagtgg ctggcggtcg ccctggcggc tggcggcgtg     420
cttctgcaac tgtggaaatt tggctcagtg ccggtgattg ccttagggct ggcgttcagc     480
ttcgcgtttt atggcctgat gaggaagaaa attcaggtcg atgcccagag cggcatgctg     540
atagagacgc tgtggctgtt tccgctggcc gcgctctatc tgtttggctt tgctgacagc     600
agcaccagcc accttagcgc gaacccatg agcctgaacc tgttactgat cgccgcaggc     660
attgttacca cgattccgct gatgttcttc gccgcgcgtt gtacccgact gcgcctgtca     720
acggtgggct tctttcagta tctgggccct acgctgatgt tcttgctggc ggtgctgttt     780
```

```
tatggtgaaa ccgttacgcc agataaaatg gtaacctttg gttttatctg gctggctctg    840
ctggtcttta ttctggatgc cgtggcgttt tcagcgcgga gccgaatgcg caaagcgtga    900
```

<210> SEQ ID NO 2
<211> LENGTH: 299
<212> TYPE: PRT
<213> ORGANISM: Pantoea ananatis

<400> SEQUENCE: 2

```
Met Asp Thr Gln Gln Thr Arg Gln Gly Ile Gly Phe Ala Leu Gly Ala
1               5                   10                  15

Tyr Phe Ile Trp Gly Ile Ala Pro Ala Tyr Phe Lys Leu Val Lys Ala
            20                  25                  30

Val Pro Ala Thr Glu Ile Met Thr His Arg Val Ile Trp Ser Ala Leu
        35                  40                  45

Phe Met Leu Leu Leu Ile Thr Leu Ser Arg Ser Trp Gly Gln Val Arg
    50                  55                  60

Ser Val Leu Arg Gln Pro Lys Lys Val Leu Leu Ala Leu Thr Ala
65                  70                  75                  80

Val Thr Val Gly Gly Asn Trp Leu Leu Phe Ile Trp Ala Val Asn Asn
                85                  90                  95

Gln His Met Leu Glu Ala Ser Leu Gly Tyr Phe Ile Asn Pro Leu Ile
            100                 105                 110

Asn Val Phe Gly Met Ile Phe Leu Arg Glu Arg Phe Arg Leu
        115                 120                 125

Gln Trp Leu Ala Val Ala Leu Ala Ala Gly Val Leu Leu Gln Leu
    130                 135                 140

Trp Lys Phe Gly Ser Val Pro Val Ile Ala Leu Gly Leu Ala Phe Ser
145                 150                 155                 160

Phe Ala Phe Tyr Gly Leu Met Arg Lys Lys Ile Gln Val Asp Ala Gln
                165                 170                 175

Ser Gly Met Leu Ile Glu Thr Leu Trp Leu Phe Pro Leu Ala Ala Leu
            180                 185                 190

Tyr Leu Phe Gly Phe Ala Asp Ser Ser Thr Ser His Leu Ser Ala Asn
        195                 200                 205

Pro Met Ser Leu Asn Leu Leu Leu Ile Ala Ala Gly Ile Val Thr Thr
    210                 215                 220

Ile Pro Leu Met Phe Phe Ala Ala Ala Cys Thr Arg Leu Arg Leu Ser
225                 230                 235                 240

Thr Val Gly Phe Phe Gln Tyr Leu Gly Pro Thr Leu Met Phe Leu Leu
                245                 250                 255

Ala Val Leu Phe Tyr Gly Glu Thr Val Thr Pro Asp Lys Met Val Thr
            260                 265                 270

Phe Gly Phe Ile Trp Leu Ala Leu Leu Val Phe Ile Leu Asp Ala Val
        275                 280                 285

Ala Phe Ser Ala Arg Ser Arg Met Arg Lys Ala
    290                 295
```

<210> SEQ ID NO 3
<211> LENGTH: 900
<212> TYPE: DNA
<213> ORGANISM: Artificial Sequence
<220> FEATURE:
<223> OTHER INFORMATION: mutant gene rarD

<400> SEQUENCE: 3

```
atggatacccc agcaaacccg tcagggcatc ggctttgcgc ttggcgctta ctttatttgg    60
ggcattgcgc cgcctactt caaattagtg aaggccgtac cggcgactga aatcatgacc     120
cacagggtga tctggtcagc actgttcatg ttgttactga ttaccctgag tcgcagttgg    180
ggacaggtca gaagcgtgct gcgccagcca aaaaaagtgc tgctactggc ccttacggcg    240
gtaacggtag ggggagactg gttgctgttt atctgggcgg tgaacaatca gcatatgctt    300
gaagccagcc tgggctattt tatcaacccg ttgattaacg ttgtgtttgg catgattttc    360
ctgcgtgaac gtttccgtcg cctgcagtgg ctggcggtcg ccctggcggc tggcggcgtg    420
cttctgcaac tgtggaaatt tggctcagtg ccggtgattg ccttagggct ggcgttcagc    480
ttcgcgtttt atggcctgat gaggaagaaa attcaggtcg atgcccagag cggcatgctg    540
atagagacgc tgtggctgtt ccgctggcc gcgctctatc tgtttggctt tgctgacagc    600
agcaccagcc accttagcgc gaaccccatg agcctgaacc tgttactgat cgccgcaggc    660
attgttacca cgattccgct gatgttcttc gccgcggctt gtacccgact gcgcctgtca    720
acggtgggct tctttcagta tctgggccct acgctgatgt tcttgctggc ggtgctgttt    780
tatggtgaaa ccgttacgcc agataaaatg gtaacctttg gttttatctg gctggctctg    840
ctggtctttta ttctggatgc cgtggcgttt cagcgcgga ccgaatgcg caaagcgtga    900
```

<210> SEQ ID NO 4
<211> LENGTH: 299
<212> TYPE: PRT
<213> ORGANISM: Artificial Sequence
<220> FEATURE:
<223> OTHER INFORMATION: mutant protein RarD (N86D)

<400> SEQUENCE: 4

```
Met Asp Thr Gln Gln Thr Arg Gln Gly Ile Gly Phe Ala Leu Gly Ala
1               5                   10                  15

Tyr Phe Ile Trp Gly Ile Ala Pro Ala Tyr Phe Lys Leu Val Lys Ala
            20                  25                  30

Val Pro Ala Thr Glu Ile Met Thr His Arg Val Ile Trp Ser Ala Leu
        35                  40                  45

Phe Met Leu Leu Leu Ile Thr Leu Ser Arg Ser Trp Gly Gln Val Arg
    50                  55                  60

Ser Val Leu Arg Gln Pro Lys Lys Val Leu Leu Ala Leu Thr Ala
65                  70                  75                  80

Val Thr Val Gly Gly Asp Trp Leu Leu Phe Ile Trp Ala Val Asn Asn
                85                  90                  95

Gln His Met Leu Glu Ala Ser Leu Gly Tyr Phe Ile Asn Pro Leu Ile
            100                 105                 110

Asn Val Val Phe Gly Met Ile Phe Leu Arg Glu Arg Phe Arg Arg Leu
        115                 120                 125

Gln Trp Leu Ala Val Ala Leu Ala Ala Gly Gly Val Leu Leu Gln Leu
    130                 135                 140

Trp Lys Phe Gly Ser Val Pro Val Ile Ala Leu Gly Leu Ala Phe Ser
145                 150                 155                 160

Phe Ala Phe Tyr Gly Leu Met Arg Lys Lys Ile Gln Val Asp Ala Gln
                165                 170                 175

Ser Gly Met Leu Ile Glu Thr Leu Trp Leu Phe Pro Leu Ala Ala Leu
            180                 185                 190

Tyr Leu Phe Gly Phe Ala Asp Ser Ser Thr Ser His Leu Ser Ala Asn
        195                 200                 205
```

```
Pro Met Ser Leu Asn Leu Leu Leu Ile Ala Ala Gly Ile Val Thr Thr
    210                 215                 220

Ile Pro Leu Met Phe Phe Ala Ala Ala Cys Thr Arg Leu Arg Leu Ser
225                 230                 235                 240

Thr Val Gly Phe Phe Gln Tyr Leu Gly Pro Thr Leu Met Phe Leu Leu
                245                 250                 255

Ala Val Leu Phe Tyr Gly Glu Thr Val Thr Pro Asp Lys Met Val Thr
                260                 265                 270

Phe Gly Phe Ile Trp Leu Ala Leu Leu Val Phe Ile Leu Asp Ala Val
            275                 280                 285

Ala Phe Ser Ala Arg Ser Arg Met Arg Lys Ala
    290                 295
```

```
<210> SEQ ID NO 5
<211> LENGTH: 60
<212> TYPE: DNA
<213> ORGANISM: Artificial Sequence
<220> FEATURE:
<223> OTHER INFORMATION: Primer P1

<400> SEQUENCE: 5 taactttttaa cttttattga ttaaggtatc ccatggtgaa gcctgctttt ttatactaag      60

<210> SEQ ID NO 6
<211> LENGTH: 60
<212> TYPE: DNA
<213> ORGANISM: Artificial Sequence
<220> FEATURE:
<223> OTHER INFORMATION: Primer P2

<400> SEQUENCE: 6
cagctcaggc tgggtttttt tatgtctgaa aatcagcgct caagttagta taaaaaagct      60

<210> SEQ ID NO 7
<211> LENGTH: 20
<212> TYPE: DNA
<213> ORGANISM: Artificial Sequence
<220> FEATURE:
<223> OTHER INFORMATION: Primer P3

<400> SEQUENCE: 7
gtgcgttgaa cgaagaaacc                                                   20

<210> SEQ ID NO 8
<211> LENGTH: 20
<212> TYPE: DNA
<213> ORGANISM: Artificial Sequence
<220> FEATURE:
<223> OTHER INFORMATION: Primer P4

<400> SEQUENCE: 8
cgcttcaaca agcgtttcag                                                   20

<210> SEQ ID NO 9
<211> LENGTH: 930
<212> TYPE: DNA
<213> ORGANISM: Pantoea ananatis

<400> SEQUENCE: 9
atgccaatca gggtccccga cgaattaccg gcagtgaatt ttttacgtaa cgaaaacgtc      60
tttgtgatga cgtcgtcacg tgccagtgtt caggagatcc gtccgcttaa agtgctggtt     120
cttaatctca tgcccaagaa gattgagaca gaaaaccagt ttctgcgctt actctctaac     180
```

-continued

```
tcaccgctgc agatcgatat ccagctactg cgcatcgaca gccgggagtc gcggaataca      240
cccagcgatc atctcaacaa cttctactgc aattttaacg atattcagca cgataactac      300
gatggcttaa tcgtgacagg tgcgccgctg ggcctggttg aatttaacga tgtggcttac      360
tggccgcaga taaaacaggt gctggagtgg gcgaaagatc atgttacctc cacgctgttt      420
gtctgttggg ccgtccaggc ggcattaaac attttatatg cattcctaa acagacccgg       480 cagactaaac tggcgggcgt cttttgagcat cagatactgc atccccattc cttactgacg      540
cggggattcg acgataattt cctcgctccc cattcacgtt acgctgattt cccgacgcag      600
ctcatcacgg attataccga tctggaatta tttgctgaat cggaacaaac cggcgcgtat      660
ctgatggcga gcaaagacaa aaggctggcg tttgtgaccg gcatccgga gtacgatgca       720 ctgacgctgg cgggagagtt caacgcgac tatgaagccg ggctgaatcc tgaagtaccc       780
tataactatt cccacagga taatccgcag cttacaccgc gcgccacctg gcgtagccat      840
ggaaacctgc tgttttcaaa ctggctgaat tattacgtct accagattac gccgtttgat      900
ctgcgccata tgaatcccac gctggaataa                                       930
```

```
<210> SEQ ID NO 10
<211> LENGTH: 309
<212> TYPE: PRT
<213> ORGANISM: Pantoea ananatis

<400> SEQUENCE: 10

Met Pro Ile Arg Val Pro Asp Glu Leu Pro Ala Val Asn Phe Leu Arg
1               5                   10                  15

Asn Glu Asn Val Phe Val Met Thr Ser Ser Arg Ala Ser Val Gln Glu
                20                  25                  30

Ile Arg Pro Leu Lys Val Leu Val Leu Asn Leu Met Pro Lys Lys Ile
            35                  40                  45

Glu Thr Glu Asn Gln Phe Leu Arg Leu Ser Asn Ser Pro Leu Gln
        50                  55                  60

Ile Asp Ile Gln Leu Leu Arg Ile Asp Ser Arg Glu Ser Arg Asn Thr
65                  70                  75                  80

Pro Ser Asp His Leu Asn Asn Phe Tyr Cys Asn Phe Asn Asp Ile Gln
                85                  90                  95

His Asp Asn Tyr Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ala Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Gln Thr Lys Leu Ala Gly Val Phe Glu His Gln Ile Leu His Pro His
                165                 170                 175

Ser Leu Leu Thr Arg Gly Phe Asp Asp Asn Phe Leu Ala Pro His Ser
            180                 185                 190

Arg Tyr Ala Asp Phe Pro Thr Gln Leu Ile Thr Asp Tyr Thr Asp Leu
        195                 200                 205

Glu Leu Phe Ala Glu Ser Glu Gln Thr Gly Ala Tyr Leu Met Ala Ser
    210                 215                 220

Lys Asp Lys Arg Leu Ala Phe Val Thr Gly His Pro Glu Tyr Asp Ala
225                 230                 235                 240
```

Leu Thr Leu Ala Gly Glu Phe Gln Arg Asp Tyr Glu Ala Gly Leu Asn
                245                 250                 255

Pro Glu Val Pro Tyr Asn Tyr Phe Pro Gln Asp Asn Pro Gln Leu Thr
            260                 265                 270

Pro Arg Ala Thr Trp Arg Ser His Gly Asn Leu Leu Phe Ser Asn Trp
        275                 280                 285

Leu Asn Tyr Tyr Val Tyr Gln Ile Thr Pro Phe Asp Leu Arg His Met
    290                 295                 300

Asn Pro Thr Leu Glu
305

<210> SEQ ID NO 11
<211> LENGTH: 930
<212> TYPE: DNA
<213> ORGANISM: Artificial Sequence
<220> FEATURE:
<223> OTHER INFORMATION: mutant gene metA

<400> SEQUENCE: 11
atgccaatca gggtccccga cgaattaccg gcagtgaatt ttttacgtaa cgaaaacgtc      60
tttgtgatga cgtcgtcacg tgccagtgtt caggagatct gtccgcttaa agtgctggtt     120
cttaatctca tgcccaagaa gattgagaca gaaaaccagt ttctgcgctt actctctaac    180
tcaccgctgc agatcgatat ccagctactg cgcatcgaca gccggagtc gcggaataca     240
cccagcgatc atctcaacaa cttctactgc aattttaacg atattcagca cgataactac    300
gatggcttaa tcgtgacagg tgcgccgctg ggcctggttg aatttaacga tgtggcttac    360
tggccgcaga taaaacaggt gctggagtgg gcgaaagatc atgttacctc cacgctgttt    420
gtctgttggg ccgtccaggc ggcattaaac attttatatg cattcctaa acagacccgg     480
cagactaaac tggcgggcgt ctttgagcat cagatactgc atccccattc cttactgacg    540
cggggattcg acgataattt cctcgctccc cattcacgtt acgctgattt cccgacgcag    600
ctcatcacgg attataccga tctggaatta tttgctgaat cggaacaaac cggcgcgtat    660
ctgatggcga gcaaagacaa aaggctggcg tttgtgaccg gcatccgga gtacgatgca     720
ctgacgctgg cgggagagtt tcaacgcgac tatgaagccg gctgaatcc tgaagtaccc    780
tataactatt tcccacagga taatccgcag cttacaccgc gcgccacctg gcgtagccat    840
ggaaacctgc tgttttcaaa ctggctgaat tattacgtct accagattac gccgtttgat    900
ctgcgccata tgaatcccac gctggaataa                                     930

<210> SEQ ID NO 12
<211> LENGTH: 309
<212> TYPE: PRT
<213> ORGANISM: Artificial Sequence
<220> FEATURE:
<223> OTHER INFORMATION: mutant protein MetA (R34C)

<400> SEQUENCE: 12

Met Pro Ile Arg Val Pro Asp Glu Leu Pro Ala Val Asn Phe Leu Arg
1               5                   10                  15

Asn Glu Asn Val Phe Val Met Thr Ser Ser Arg Ala Ser Val Gln Glu
            20                  25                  30

Ile Cys Pro Leu Lys Val Leu Val Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

```
Ile Asp Ile Gln Leu Leu Arg Ile Asp Ser Arg Glu Ser Arg Asn Thr
 65                  70                  75                  80

Pro Ser Asp His Leu Asn Asn Phe Tyr Cys Asn Phe Asn Asp Ile Gln
             85                  90                  95

His Asp Asn Tyr Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
            115                 120                 125

Glu Trp Ala Lys Asp His Val Thr Ser Thr Leu Phe Val Cys Trp Ala
        130                 135                 140

Val Gln Ala Ala Leu Asn Ile Leu Tyr Gly Ile Pro Lys Gln Thr Arg
145                 150                 155                 160

Gln Thr Lys Leu Ala Gly Val Phe Glu His Gln Ile Leu His Pro His
                165                 170                 175

Ser Leu Leu Thr Arg Gly Phe Asp Asp Asn Phe Leu Ala Pro His Ser
            180                 185                 190

Arg Tyr Ala Asp Phe Pro Thr Gln Leu Ile Thr Asp Tyr Thr Asp Leu
        195                 200                 205

Glu Leu Phe Ala Glu Ser Glu Gln Thr Gly Ala Tyr Leu Met Ala Ser
    210                 215                 220

Lys Asp Lys Arg Leu Ala Phe Val Thr Gly His Pro Glu Tyr Asp Ala
225                 230                 235                 240

Leu Thr Leu Ala Gly Glu Phe Gln Arg Asp Tyr Glu Ala Gly Leu Asn
                245                 250                 255

Pro Glu Val Pro Tyr Asn Tyr Phe Pro Gln Asp Asn Pro Gln Leu Thr
            260                 265                 270

Pro Arg Ala Thr Trp Arg Ser His Gly Asn Leu Leu Phe Ser Asn Trp
        275                 280                 285

Leu Asn Tyr Tyr Val Tyr Gln Ile Thr Pro Phe Asp Leu Arg His Met
    290                 295                 300

Asn Pro Thr Leu Glu
305

<210> SEQ ID NO 13
<211> LENGTH: 33
<212> TYPE: DNA
<213> ORGANISM: Artificial Sequence
<220> FEATURE:
<223> OTHER INFORMATION: Primer P5

<400> SEQUENCE: 13
agctgagcat gcaaaacgtg aggaaatacc tgg                                33

<210> SEQ ID NO 14
<211> LENGTH: 34
<212> TYPE: DNA
<213> ORGANISM: Artificial Sequence
<220> FEATURE:
<223> OTHER INFORMATION: Primer P6

<400> SEQUENCE: 14
agctgagtcg acggagcacc agtatttgaa acgg                               34

<210> SEQ ID NO 15
<211> LENGTH: 31
<212> TYPE: DNA
<213> ORGANISM: Artificial Sequence
<220> FEATURE:
```

```
<223> OTHER INFORMATION: Primer P7

<400> SEQUENCE: 15
agctgagtcg acatggatac ccagcaaacc c                              31

<210> SEQ ID NO 16
<211> LENGTH: 32
<212> TYPE: DNA
<213> ORGANISM: Artificial Sequence
<220> FEATURE:
<223> OTHER INFORMATION: Primer P8

<400> SEQUENCE: 16
agctgatcta gatttcacgc tttgcgcatt cg                             32
```

METHOD FOR PRODUCING L-METHIONINE USING A BACTERIUM OF THE GENUS *PANTOEA*

This application is a Continuation of, and claims priority under 35 U.S.C. § 120 to, International Application No. PCT/JP2019/018057, filed Apr. 26, 2019, and claims priority therethrough under 35 U.S.C. § 119 to Russian Patent Application No. 2018116608, filed May 4, 2018, the entireties of which are incorporated by reference herein. Also, the Sequence Listing filed electronically herewith is hereby incorporated by reference (File name: 2020-10-27T_US-619_Seq_List; File size: 18 KB; Date recorded: Oct. 27, 2020).

BACKGROUND

General Field

The present invention relates generally to the microbiological industry, and specifically to a method for producing L-methionine by fermentation of a bacterium of the genus *Pantoea* which has been modified to overexpress the rarD gene, so that production of the L-methionine is enhanced.

Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acids production yields have been reported, including transformation of microorganisms with recombinant DNA (see, for example, U.S. Pat. No. 4,278,765 A) and alteration of expression regulatory regions such as promoters, leader sequences, and/or attenuators, or others known to the person skilled in the art (see, for example, US20060216796 A1 and WO9615246 A1). Other techniques for enhancing production yields include increasing the activities of enzymes involved in amino acid biosynthesis and/or desensitizing the target enzymes to the feedback inhibition by the resulting L-amino acid (see, for example, WO9516042 A1, EP0685555 A1 or U.S. Pat. Nos. 4,346,170 A, 5,661,012 A, and 6,040,160 A).

Another method for enhancing L-amino acids production yields is to attenuate expression of a gene or several genes which are involved in degradation of the target L-amino acid, genes which divert the precursors of the target L-amino acid from the L-amino acid biosynthetic pathway, genes involved in the redistribution of the carbon, nitrogen, sulfur, and phosphate fluxes, and genes encoding toxins, etc.

As for L-methionine, also known as (2S)-2-amino-4-(methylsulfanyl) butanoic acid, a method for producing L-methionine by culturing in a medium a recombinant *Escherichia* bacterium that is deficient, at least, in a repressor of L-methionine biosynthesis system encoded by the metJ gene, is known (U.S. Pat. No. 7,611,873 B1). The bacterium used in the method was modified further to increase activity of intracellular homoserine transsuccinylase (MetA). Moreover, the homoserine transsucinylase of the bacterium that was used in the method for producing L-methionine has been modified to render it insensitive to the feedback inhibition by L-methionine. Specifically, the amino acid sequence of the MetA in the *Escherichia* bacterium was modified to contain, at least, one of the following substitutions: replacing the arginine (Arg) residue at position 27 with a cysteine (Cys) residue (R27C mutation), the isoleucine (Ile) residue at position 296 with a serine (Ser) residue (I296S mutation), and the proline (Pro) residue at position 298 with a leucine (Leu) residue (P298L mutation).

In another example, a recombinant microorganism, which may be a bacterium belonging to the family Enterobacteriaceae or Corynebacteriaceae, was modified in order to improve the fermentative production of L-methionine, such that the activity of the cobalamin-independent methionine synthase (MetE) is suppressed and the metH gene is overexpressed in the microorganism (EP2861726 B1; as for the use of enhanced 5-methyltetrahydrofolate homocysteine methyltransferase (MetH), see also, for example, WO0210209 A1).

Other methods for producing L-methionine by fermentation of a bacterium are known, including, for example, the method in which a bacterial strain having the ability to produce L-threonine and transformed with vector(s) expressing threonine dehydratase (tdcB, ilvA) and, at least, O-succinylhomoserine lyase (metB), cystathionine beta-lyase (metC), 5,10-methylenetetrahydrofolate reductase (metF) and serine hydroxymethyltransferase (glyA) was used (U.S. Pat. No. 7,790,424 B2); the method in which a microorganism of the Enterobacteriaceae family modified to enhance the transhydrogenase activity of PntAB was used (EP2633037 B1); and so forth.

A method is also disclosed for producing an L-amino acid using a microorganism in which activity of a RarD protein native to *Escherichia coli* (*E. coli*) species or an 80% or higher homologous variant thereof is enhanced, wherein the microorganism belongs to the genus *Escherichia*, *Corynebacterium*, *Bacillus*, *Serratia*, *Pseudomonas* or *Streptomyces*, and wherein the L-amino acid is, particularly, L-serine, L-glutamine, L-cysteine, L-phenylalanine, and L-threonine (US2012015409 A1). The RarD protein (synonym: YigH) native to *E. coli* is characterized as a putative member of drug/metabolite transporter superfamily (EcoCyc database, ecocyc.org, accession ID: EG11466). In the Transporter Classification Database, RarD is classified as a member of the Chloramphenicol-Sensitivity Protein (RarD) Family within the Drug/Metabolite Transporter (DMT) superfamily (Saier M. H. Jr. et al., The Transporter Classification Database (TCDB): recent advances, *Nucleic Acids Res.*, 2016, 44(D1):D372-9; doi: 10.1093/nar/gkv1103).

However, no data has been previously reported that describes the effect of overexpression of the rarD gene native to *Pantoea* species or a variant thereof on production of L-methionine by fermentation of an L-methionine-producing bacterium of the genus *Pantoea*.

SUMMARY

An improved method of producing L-methionine by fermentation of a bacterium of the genus *Pantoea* is described herein. According to the presently disclosed subject matter, production of L-methionine by fermentation of a bacterium of the genus *Pantoea* can be increased. Specifically, production of L-methionine by fermentation of a bacterium of the genus *Pantoea* can be improved by overexpressing the rarD gene in the bacterium, so that the production of L-methionine by the modified bacterium can be enhanced. The production of L-methionine by fermentation of a bacterium of the genus *Pantoea* can be enhanced further by overexpressing in the bacterium the mutant rarD gene encoding the mutant RarD protein having the replacement of the asparagine (Asn) residue at position 86 with an acidic amino acid residue such as the aspartic acid (Asp) residue (N86D mutation) or the glutamic acid (Glu) residue (N86E mutation) in the amino acid sequence of the RarD. Moreover, the production of L-methionine by fermentation of a bacterium of the genus *Pantoea* can be enhanced further by modifying the amino acid sequence of homoserine transsuccinylase (MetA) in the bacterium such that the homoserine transsuccinylase is devoid of the feedback inhibition by L-methionine. Specifically, the MetA protein native to the bacterium was modified to contain the replacement of the arginine (Arg) residue at position 34 with cysteine (Cys) residue (R34C mutation) in the amino acid sequence of the MetA.

It is an aspect of the present invention to provide a method for producing L-methionine comprising: (i) cultivating in a culture medium a bacterium of the genus *Pantoea* which has an ability to produce L-methionine to produce and accumulate the L-methionine in the culture medium or the bacterial cells, or both, and (ii) collecting the L-methionine from the culture medium or the bacterial cells, or both, wherein said bacterium has been modified to overexpress a rarD gene.

It is another aspect of the present invention to provide the method as described above, wherein said rarD gene is selected from the group consisting of: (A) a DNA comprising the nucleotide sequence shown in SEQ ID NO: 1, (B) a DNA encoding a protein comprising the amino acid sequence shown in SEQ ID NO: 2, (C) a DNA encoding a protein comprising the amino acid sequence shown in SEQ ID NO: 2, but wherein said amino acid sequence includes substitution, deletion, insertion, and/or addition of about 1 to 30 amino acid residues, and wherein said protein has the activity of a protein having the amino acid sequence shown in SEQ ID NO: 2, (D) a DNA encoding a protein having an identity of not less than 90% with respect to the entire amino acid sequence shown in SEQ ID NO: 2 and having the activity of a protein having the amino acid sequence shown in SEQ ID NO: 2, and (E) a DNA comprising difference(s) in the nucleotide sequence shown in SEQ ID NO: 1, wherein the difference(s) is/are a result of the degeneracy of the genetic code.

It is another aspect of the present invention to provide the method as described above, wherein said rarD gene is overexpressed by increasing the copy number of the rarD gene and/or by modifying an expression regulatory region of the rarD gene, so that the expression of said gene is enhanced as compared with a non-modified bacterium.

It is another aspect of the present invention to provide the method as described above, wherein said rarD gene encodes a RarD protein having an amino acid substitution, wherein the asparagine residue at position 86 is replaced with an acidic amino acid residue.

It is another aspect of the present invention to provide the method as described above, wherein said acidic amino acid residue is an aspartic acid residue or a glutamic acid residue.

It is another aspect of the present invention to provide the method as described above, wherein said bacterium has been modified further to comprise a metA gene encoding a MetA protein, wherein the amino acid sequence of the MetA protein has the amino acid substitution R34C.

It is another aspect of the present invention to provide the method as described above, wherein said bacterium is *Pantoea ananatis*.

Still other objects, features, and attendant advantages of the present invention will become apparent to those skilled in the art from a reading of the following detailed description of embodiments constructed in accordance therewith.

DETAILED DESCRIPTION

1. Bacterium

Any L-methionine-producing bacterium belonging to the genus *Pantoea* can be used in the method as described herein, provided that the bacterium can be modified to overexpress the rarD gene. It is also acceptable that any L-methionine-producing bacterium belonging to the genus *Pantoea* can be used in the method as described herein, provided that the bacterium can be modified to overexpress the rarD gene, so that the production of L-methionine by the bacterium can be enhanced as compared with a non-modified bacterium. The phrase "an L-methionine-producing bacterium" can mean a bacterium of the genus *Pantoea* which has an ability to produce, excrete or secrete, and/or cause accumulation of L-methionine in a culture medium and/or the bacterial cells when the bacterium is cultured in the medium.

The phrase "an L-methionine-producing bacterium" can also mean a bacterium which has an ability to produce, excrete or secrete, and/or cause accumulation of L-methionine in a culture medium in an amount larger than a wild-type or parental strain such as, for example, *Pantoea ananatis* (*P. ananatis*) AJ13355 strain. The phrase "an L-methionine-producing bacterium" can also mean a bacterium that is able to cause accumulation in the medium of an amount, for example, not less than 0.1 g/L, not less than 0.5 g/L, or not less than 1.0 g/L of the target L-methionine.

Furthermore, the bacterium belonging to the genus *Pantoea* and modified to overexpress the rarD gene, which has an ability to produce L-methionine, can also be used. The bacterium may inherently have the ability to produce L-methionine or may be modified to have an ability to produce L-methionine by using a mutation method or DNA recombination techniques. The bacterium can be obtained by overexpressing the rarD gene in a bacterium that inherently has the ability to produce L-methionine, or in a bacterium that has been already imparted with the ability to produce L-methionine. Alternatively, the bacterium can be obtained by imparting the ability to produce L-methionine to a bacterium already modified to overexpress the rarD gene. Alternatively, the bacterium may have been imparted with the ability to produce L-methionine by being modified to overexpress the rarD gene.

The phrase "an ability to produce L-methionine" can mean the ability of a bacterium of the genus *Pantoea* to produce, excrete or secrete, and/or cause accumulation of L-methionine in a culture medium and/or the bacterial cells to such a level that the L-methionine can be collected from the culture medium and/or the bacterial cells when the bacterium is cultured in the medium. The phrase "cultured" with reference to a bacterium which is grown in a medium and used according to the method as described herein may be used interchangeably or equivalently to the phrase "cultivated", or the like, that are well-known to the persons skilled in the art.

The bacterium can produce L-methionine either alone or as a mixture of L-methionine and one or more kinds of amino acids that are different from the L-methionine such as, for example, amino acids in L-form (also referred to as L-amino acids). Furthermore, the bacterium can produce L-methionine either alone or as a mixture of L-methionine and one or more kinds of other organic acids such as, for example, carboxylic acids. Examples of L-amino acids include, but are not limited to, L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine. Examples of carboxylic acids include, but are not limited to, formic acid, acetic acid, citric acid, butyric acid, lactic acid, and propionic acid, and derivatives thereof.

The phrases "L-methionine", "L-amino acid", and "carboxylic acid" can refer not only to L-methionine, an amino acid, and a carboxylic acid in a free form, but may also include a salt or a hydrate of them, or an adduct formed by L-methionine, the amino acid, or the carboxylic acid and another organic or inorganic compound. That is, the phrases "L-methionine", "L-amino acid", and "carboxylic acid" can mean, for example, L-methionine, an amino acid, and a carboxylic acid in a free form, a hydrate of them, an adduct of them, or a mixture of them. The phrases "L-methionine", "L-amino acid", and "carboxylic acid" can include, for example, sodium, potassium, ammonium, mono-, di- and trihydrate, mono- and dichlorhydrate, and so forth salts and inner salts such as zwitterion of L-methionine, an amino acid, and a carboxylic acid. L-methionine can be produced particularly in a free form or as a salt thereof, or as a mixture of them. That is, the phrase "L-methionine" can particularly mean, for example, L-methionine in a free form, a salt form thereof, or a mixture thereof.

As the bacterium belonging to the genus *Pantoea*, any bacterium that is classified into the genus *Pantoea* according to the taxonomy used in the NCBI (National Center for Biotechnology Information) database (ncbi.nlm.nih.gov/Taxonomy/Browser/wwwtax.cgi?mode=Tree&id=53335&lvl=3&keep=1&srchmode=1&unlock) can be used. Examples of the *Pantoea* bacteria include *Pantoea ananatis* (*P. ananatis*), and so forth. Some strains of *Enterobacter agglomerans* were recently reclassified into *Pantoea agglomerans*, *Pantoea ananatis* or *Pantoea stewartii* on the basis of nucleotide sequence analysis of 16S rRNA, etc. A bacterium belonging to either genus *Enterobacter* or *Pantoea* may be used so long as it is a bacterium classified into the genus *Pantoea*. When a *Pantoea ananatis* strain is bred by genetic engineering techniques, *Pantoea ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above. The bacterial strains are available from, for example, the American Type Culture Collection (ATCC; Address: P.O. Box 1549, Manassas, Va. 20108, United States of America). That is, registration numbers are assigned to the respective strains, and the strains can be ordered by using these registration numbers (refer to lgcstandards-atcc.org). The registration numbers of the strains are listed in the catalogue of the American Type Culture Collection.

L-Methionine-Producing Bacteria

An example of L-methionine-producing bacteria of the genus *Pantoea* and parent strains thereof that can be used to derive L-methionine-producing bacteria includes, but is not limited to, *P. ananatis* strain AJ13355 (FERM BP-6614). This strain is also known as *P. ananatis* strain SC17 (FERM BP-11091), and it was isolated from soil in Iwata-shi (Shizuoka, Japan) as a bacterium that is able to grow at acidic pH and showing resistance to high concentrations of glutamic acid (U.S. Pat. No. 7,319,025 B2; Katashkina J. I. et al., Use of the λ Red-recombineering method for genetic engineering of *Pantoea ananatis*, BMC Mol. Biol., 2009, 10:34). The *P. ananatis* SC17(0) strain (VKPM B-9246) may also be used. The SC17(0) strain was constructed as a strain resistant to the λ Red gene products for performing gene disruption in *P. ananatis* (WO2008/075483).

The rarD gene of *P. ananatis* encodes a chloramphenicol resistance permease RarD (BioCyc database, biocyc.org/, accession ID: G1H69-3687; UniProtKB/Swiss-Prot database, accession No. A0A0H3L1X8; KEGG, Kyoto Encyclopedia of Genes and Genomes, entry No. PAJ_3332). The rarD gene native to *P. ananatis* has the nucleotide sequence shown in SEQ ID NO: 1, and the amino acid sequence of the RarD protein encoded by this gene is shown in SEQ ID NO: 2.

That is, the rarD gene may have the nucleotide sequence of SEQ ID NO: 1, and the RarD protein may have the amino acid sequence of SEQ ID NO: 2. The phrase "a gene or protein has a nucleotide or amino acid sequence" means that a gene or protein includes the nucleotide or amino acid sequence, possibly among a larger sequence, unless otherwise stated, and also includes cases where a gene or protein includes only the nucleotide or amino acid sequence.

There may be some differences in DNA sequences between the species or strains of the bacteria belonging to the genus *Pantoea*. Therefore, the rarD gene is not limited to the gene having the nucleotide sequence shown in SEQ ID NO: 1, but may include genes which have a variant nucleotide sequences of SEQ ID NO: 1, provided that the gene encodes a RarD protein. Similarly, the RarD protein is not limited to the protein having the amino acid sequence shown in SEQ ID NO: 2, but may include proteins which have a variant amino acid sequences of SEQ ID NO: 2, provided that the protein has a function of the RarD protein. Examples of such variant nucleotide sequences or variant proteins may include homologues of and artificially modified ones of the rarD gene or RarD protein exemplified above. Such homologous may include the rarD genes or RarD proteins native to other species of the genus *Pantoea*.

The phrase "a variant nucleotide sequence" can mean a nucleotide sequence which encodes a RarD protein using any synonymous amino acid codons according to the standard genetic code table (see, for example, Lewin B., "Genes VIII", 2004, Pearson Education, Inc., Upper Saddle River, N.J. 07458). Therefore, the rarD gene can be a gene having a variant nucleotide sequence of SEQ ID NO: 1 due to the degeneracy of the genetic code.

The phrase "a variant nucleotide sequence" can also mean a nucleotide sequence that is able to hybridize under stringent conditions with the nucleotide sequence complementary to the sequence shown in SEQ ID NO: 1 or a probe that can be prepared from the nucleotide sequence provided that it encodes a protein that maintains the activity or function of the non-modified RarD protein such as, for example, the RarD protein native to *P. ananatis*, which may be a protein having the amino acid sequence shown in SEQ ID NO: 2, or the three-dimensional structure of the protein is not significantly changed relative to the non-modified RarD protein such as, for example, the RarD protein native to *P. ananatis*. The phrase "stringent conditions" can include those conditions under which a specific hybrid, for example, a hybrid having homology, defined as the parameter "identity" when using the computer program BLAST, not less than 85%, not less than 90%, not less than 91%, not less than 92%, not less than 93%, not less than 94%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate) at 60° C., 0.1×SSC, 0.1% SDS at 60° C., or 0.1×SSC, 0.1% SDS at 65° C. Duration of washing can depend on the type of membrane used for the blotting and, as a rule, should be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequence shown in SEQ ID NO: 1 may also be used. Such a probe can be produced by PCR (polymerase chain reaction; refer to White T. J. et al., The polymerase chain reaction, *Trends Genet.,* 1989, 5:185-189) using oligonucleotides as primers prepared on the basis of the sequence shown in SEQ ID NO: 1 and a DNA fragment containing the nucleotide sequence to be used as the probe as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after the hybridization can be, for example, 2×SSC, 0.1% SDS at 50° C., 60° C. or 65° C.

The phrase "a variant nucleotide sequence" can also mean a nucleotide sequence that encodes a variant protein of the RarD protein.

The phrase "a variant protein" can mean a protein which has one or more mutations in the sequence as compared with the amino acid sequence shown in SEQ ID NO: 2, whether they are substitutions, deletions, insertions, and/or additions of one or several amino acid residues, but which still maintains the activity or function of the non-modified RarD protein such as, for example, the RarD protein native to *P. ananatis*, which may be a protein having the amino acid sequence shown in SEQ ID NO: 2, or of which the three-dimensional structure is not significantly changed relative to the non-modified RarD protein such as, for example, the RarD protein native to *P. ananatis*. The number of changes in the variant protein depends on the position of amino acid residue(s) in the three-dimensional structure of the protein or the type of amino acid residue(s). It can be, but is not strictly limited to, 1 to 30, in another example 1 to 20, in another example 1 to 15, in another example 1 to 10, and in another example 1 to 5, in SEQ ID NO: 2. This is possible because amino acids can have high homology to one another, so that the activity or function of a protein cannot be affected by a change between such amino acids, or so that the three-dimensional structure of a protein cannot be significantly changed relative to the corresponding non-modified protein by a change between such amino acids. Therefore, the variant protein may be a protein having an amino acid sequence having a homology, defined as the parameter "identity" when using the computer program BLAST, not less than 85%, not less than 90%, not less than 91%, not less than 92%, not less than 93%, not less than 94%, not less than 95%, not less than 96%, not less than 97%, not less than 98%, or not less than 99% with respect to the entire amino acid sequence shown in SEQ ID NO: 2 as long as activity or function of the RarD protein is maintained, or the three-dimensional structure of the protein is not significantly changed relative to the non-modified RarD protein such as, for example, the RarD protein native to *P. ananatis*.

The exemplary substitution, deletion, insertion, and/or addition of one or several amino acid residues can be a conservative mutation(s). The representative conservative mutation can be a conservative substitution. The conservative substitution can be, but is not limited to, a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. In addition, such substitution, deletion, insertion, addition or the like of amino acid residues as mentioned above includes a naturally occurring mutation due to an individual difference of an organism to which the amino acid sequence is native.

The exemplary substitution, deletion, insertion, and/or addition of one or several amino acid residues can also be a non-conservative mutation(s) provided that the mutation(s) is/are compensated by one or more secondary mutation(s) in the different position(s) of amino acids sequence so that activity or function of the variant protein is maintained, or the three-dimensional structure of the protein is not significantly changed relative to the non-modified protein such as, for example, the RarD protein native to *P. ananatis*.

The phrase "the activity of a protein having the amino acid sequence shown in SEQ ID NO: 2" can mean the activity of the permease protein RarD that can confer on a bacterium the resistance to chloramphenicol. It is known that there are membrane proteins that can confer on a bacterium the resistance to target compounds such as, for example, analogs of amino acids (Doroshenko V. et al., YddG from *Escherichia coli* promotes export of aromatic amino acids, *FEMS Microbiol. Lett.,* 2007, 275(2):312-318). Methods for determining the activity of transporter proteins that can confer on a bacterium the resistance to a target compound are known, and those methods can be similarly used to determine the activity of a protein having the amino acid sequence shown in SEQ ID NO: 2, in which, for example, the minimal inhibitory concentration (MIC) is determined for the protein towards the target compound (see, for example, Doroshenko V. et al., 2007; Livshits V. A. et al., Identification and characterization of the new gene rhtA involved in threonine and homoserine efflux in *Escherichia coli, Res. Microbiol.,* 2003, 154(2):123-135). The protein concentration can be determined by the Bradford protein assay using bovine serum albumin as a standard (Bradford M. M., *Anal. Biochem.*, 1976, 72:248-254).

Since the nucleotide sequence of the rarD gene encoding the RarD protein native to the species *P. ananatis* has already been elucidated (see above), the rarD gene native to *P. ananatis* or a variant nucleotide sequence thereof can be obtained by cloning from *P. ananatis* by PCR (polymerase chain reaction; refer to White T. J. et al., The polymerase chain reaction, *Trends Genet.*, 1989, 5:185-189) utilizing primers prepared based on the nucleotide sequence of the rarD gene native to *P. ananatis*; a mutagenesis method of treating a DNA containing the rarD gene native to *P. ananatis* in vitro, for example, with hydroxylamine, or a mutagenesis method of treating *P. ananatis* harboring the rarD gene with ultraviolet (UV) irradiation or a mutating agent such as N-methyl-N'-nitro-N-nitrosoguanidine (NTG) and nitrous acid usually used for the such treatment; or chemical synthesis as a full-length gene structure. Genes encoding the RarD proteins native to other species of the genus *Pantoea* and variant nucleotide sequences thereof can be obtained in a similar manner.

Moreover, the rarD gene may encode the RarD protein, wherein the asparagine (Asn) residue at position 86 is replaced with an acidic amino acid residue, which may be the aspartic acid (Asp, D) residue (N86D mutation) or the glutamic acid (Glu, E) residue (N86E mutation), in the amino acid sequence of a wild-type RarD protein, so that to enhance further the production of L-methionine using the bacterium as described herein. The mutation at position 86 may particularly be the N86D mutation. The RarD protein having the mutation at position 86 is also referred to as "a mutant RarD protein". The rarD gene encoding a mutant RarD protein is also referred to as "a mutant rarD gene". The phrase "a wild-type RarD protein" can refer to a RarD protein not having the mutation at position 86. A rarD gene encoding a mutant RarD protein is also referred to as "a wild-type rarD gene". Examples of the wild-type rarD gene can include the rarD gene native to *P. ananatis* and variants thereof provided that the variants do not have a mutation resulting in the mutation at position 86 of the encoded protein. Examples of the wild-type RarD protein can include the RarD protein native to *P. ananatis* and variants thereof provided that the variants do not have the mutation at position 86. In other words, the mutant rarD gene may be identical to any wild-type rarD gene, except that the mutant rarD gene has a mutation resulting in the mutation at position 86 of the encoded protein. Also, the mutant RarD protein may be identical to any wild-type RarD protein, except that the mutant RarD protein has the mutation at position 86. Specifically, the amino acid sequence of the mutant RarD protein can be as shown in SEQ ID NO: 4, that is encoded by the mutant rarD gene having the nucleotide sequence shown in SEQ ID NO: 3. That is, the rarD gene, specifically the mutant rarD gene, may have the nucleotide sequence of SEQ ID NO: 3, and the RarD protein, specifically the mutant RarD protein, may have the amino acid sequence of SEQ ID NO: 4. The rarD gene, specifically the mutant rarD gene, may also have a variant nucleotide sequence of SEQ ID NO: 3, provided that the variant nucleotide sequence has a mutation resulting in the mutation at position 86 of the encoded protein. The RarD protein, specifically the mutant RarD protein, may also have a variant amino acid sequence of SEQ ID NO: 4, provided that the variant amino acid sequence has the mutation at position 86 of the encoded protein.

The phrase "the asparagine (Asn) residue at position 86 in the amino acid sequence of a wild-type RarD protein" in the amino acid sequence of any chosen wild-type RarD protein can refer to an amino acid residue corresponding to the Asn residue at position 86 in the amino acid sequence shown as SEQ ID NO: 2 in an alignment of the amino acid sequence of the chosen wild-type RarD protein and the amino acid sequence of SEQ ID NO: 2. That is, the phrase "position 86" does not necessarily indicate an absolute position in the amino acid sequence of a wild-type RarD protein, but indicates a relative position based on the amino acid sequence shown as SEQ ID NO: 2. For example, when one amino acid residue is deleted at a position on the N-terminus side of the Asn residue at position 86 in the amino acid sequence shown as SEQ ID NO: 2, the Asn residue originally at position 86 becomes the Asn residue at position 85 in the resulting amino acid sequence, but it is still regarded as "the Asn residue at position 86 in the amino acid sequence of a wild-type RarD protein". Such alignment can be performed by, for example, using known gene analysis software. Specific examples of such software include DNASIS produced by Hitachi Solutions, GENETYX produced by Genetyx, ClustalW opened to the public by DDBJ, and so forth (Elizabeth C. Tyler et al., Computers and Biomedical Research, 24(1), 72-96, 1991; Barton G. J. et al., Journal of Molecular Biology, 198 (2), 327-37, 1987; Thompson J D et al., Nucleic Acid Research, 22 (22), 4673-80, 1994).

The mutant rarD gene can be obtained by, for example, modifying the wild-type rarD gene so that the encoded protein has the mutation at position 86. The wild-type rarD gene to be modified can be obtained as described above, for example, by cloning from *Pantoea* bacteria having the wild-type rarD gene, or chemical synthesis. Modification of a gene can be performed by a known method. For example, by the site-specific mutagenesis method, an objective mutation can be introduced into a target site of DNA. Examples of the site-specific mutagenesis method include a method of using PCR (Higuchi, R., 61, in PCR Technology, Erlich, H. A. Eds., Stockton Press, 1989; Carter P., Meth., in Enzymol., 154, 382, 1987), and a method of using a phage (Kramer, W. and Frits, H. J., Meth. in Enzymol., 154, 350, 1987; Kunkel, T. A. et al., Meth. in Enzymol., 154, 367, 1987). Furthermore, the mutant rarD gene can also be obtained without using the wild-type rarD gene. For example, the mutant rarD gene may be directly obtained by chemical synthesis.

To evaluate the degree of protein or DNA homology, several calculation methods can be used, such as a BLAST search, FASTA search and ClustalW method. The BLAST (Basic Local Alignment Search Tool, ncbi.nlm.nih.gov/BLAST/) search is the heuristic search algorithm employed by the programs blastp, blastn, blastx, megablast, tblastn, and tblastx; these programs ascribe significance to their findings using the statistical methods of Karlin S. and Altschul S. F. ("Methods for assessing the statistical significance of molecular sequence features by using general scoring schemes", *Proc. Natl. Acad. Sci. USA*, 1990, 87:2264-2268; "Applications and statistics for multiple high-scoring segments in molecular sequences", *Proc. Natl. Acad. Sci. USA*, 1993, 90:5873-5877). The computer program BLAST calculates three parameters: score, identity and similarity. The FASTA search method is described by Pearson W. R. ("Rapid and sensitive sequence comparison with FASTP and FASTA", *Methods Enzymol.*, 1990, 183: 63-98). The ClustalW method is described by Thompson J. D. et al. ("CLUSTAL W: improving the sensitivity of progressive multiple sequence alignment through sequence weighting, position-specific gap penalties and weight matrix choice", *Nucleic Acids Res.*, 1994, 22:4673-4680). In this specification, the phrase "homology" may mean "identity", which is the identity of amino acid sequences or nucleotide sequences. The sequence identity between two sequences is calculated as the ratio of residues matching in the two sequences when aligning the two sequences so as to achieve a maximum alignment with each other. The phrase "identity" between amino acid sequences may specifically mean an identity calculated by blastp with default scoring parameters (i.e. Matrix, BLOSUM62; Gap Costs, Existence=11, Extension=1; Compositional Adjustments, Conditional compositional score matrix adjustment), unless otherwise stated. The phrase "identity" between nucleotide sequences may specifically mean an identity calculated by blastn with default scoring parameters (i.e. Match/Mismatch Scores=1, −2; Gap Costs=Linear), unless otherwise stated.

The phrase "a bacterium has been modified to overexpress the rarD gene" can mean that the bacterium has been modified in such a way that in the modified bacterium the total amount and/or the total activity of the corresponding gene product, which is the RarD protein, is increased as compared with, or the expression level (i.e. expression amount) of the rarD gene is higher than that level in, a non-modified bacterium. The phrase "a non-modified bacterium" can refer to a bacterial strain that can serve as a reference for the above comparison. The phrase "a non-modified bacterium" is also referred to as "a non-modified strain" or "a non-modified bacterial strain". Examples of the non-modified bacterial strain can include a wild-type or parental strain of a bacterium belonging to the genus Pantoea such as Pantoea ananatis. Specific examples of the non-modified bacterial strain can include the P. ananatis AJ13355 strain (FERM BP-6614).

The phrase "the rarD gene is overexpressed" can mean that the total amount and/or the total activity of the corresponding gene product, which is the RarD protein, is increased as compared with a non-modified bacterial strain. The total amount and/or the total activity of the corresponding gene product, which is the RarD protein, can be increased by, for example, increasing (i.e. enhancing) the expression level of the rarD gene, or increasing the activity per molecule (may be referred to as a specific activity) of the protein encoded by the rarD gene, as compared with a non-modified bacterial strain. An increase in the total amount or total activity of the RarD protein can be measured as, for example, an increase in the amount and/or the activity of the RarD protein per cell, which may be an average amount and/or activity of the RarD protein per cell. The bacterium can be modified so that the amount and/or the activity of the RarD protein per cell is increased to 150% or more, 200% or more, or 300% or more, of the amount and/or the activity in a non-modified bacterial strain.

The phrase "the rarD gene is overexpressed" can also mean that the expression level (i.e. expression amount) of the rarD gene is higher than that level in a non-modified bacterial strain. Therefore, the phrase "the rarD gene is overexpressed" can be used interchangeably or equivalently to the phrase "expression of the rarD gene is enhanced or increased". An increase in the expression level of the rarD gene can be measured as, for example, an increase in the expression level of the rarD gene per cell, which may be an average expression level of the rarD gene per cell. The bacterium can be modified so that the expression level of the rarD gene per cell is increased to 150% or more, 200% or more, or 300% or more, of the expression level in a non-modified bacterial strain.

Methods which can be used to enhance expression of the rarD gene include, but are not limited to, increasing the copy number of the rarD gene, such as the copy number of the rarD gene in the chromosome of the bacterium and/or in the autonomously replicating plasmid harbored by the bacterium. The copy number of the rarD gene can be increased by, for example, introducing the gene into the chromosome of the bacterium and/or introducing an autonomously replicating vector containing the rarD gene into the bacterium. Such modification of a bacterium of the genus Pantoea can be carried out according to genetic engineering methods which are well-known to the persons skilled in the art.

Examples of the vectors include, but are not limited to, broad-host-range plasmids such as pMW118/119, pBR322, pUC19, and the like. The rarD gene can also be introduced into the chromosomal DNA of a bacterium by, for example, homologous recombination, Mu-driven integration, or the like. Only one copy, or two or more copies of the rarD gene may be introduced. For example, homologous recombination can be carried out using sequence with multiple copies in the chromosomal DNA to introduce multiple copies of the rarD gene into the chromosomal DNA. Sequences with multiple copies in the chromosomal DNA include, but are not limited to, repetitive DNA or inverted repeats present at the end of a transposable element. In addition, it is possible to incorporate the rarD gene into a transposon and allow it to be transferred to introduce multiple copies of the rarD gene into the chromosomal DNA.

The further methods which can be used to enhance expression of the rarD gene include increasing the expression level of the rarD gene by modification of expression regulatory region(s) of the rarD gene. Expression regulatory region(s) of the rarD gene can be modified by, for example, replacing the native expression regulatory region(s) of the rarD gene with native and/or modified foreign regulatory region(s). The phrase "an expression regulatory region" can also be referred to as "an expression regulatory sequence". Expression regulatory regions can be exemplified by promoters, enhancers, attenuators and termination signals, anti-termination signals, ribosome-binding sites (RBS) and other expression control elements (e.g., regions to which repressors or inducers bind and/or binding sites for transcriptional and translational regulatory proteins, for example, in the transcribed mRNA). Such regulatory regions are described, for example, in Sambrook J., Fritsch E. F. and Maniatis T., "Molecular Cloning: A Laboratory Manual", $2^{nd}$ ed., Cold Spring Harbor Laboratory Press (1989). Modification of expression regulatory region(s) of the rarD gene can be combined with increasing the copy number of the rarD gene (see, for example, Akhverdyan V. Z. et al., Appl. Microbiol. Biotechnol., 2011, 91:857-871; Tyo K. E. J. et al., Nature Biotechnol., 2009, 27:760-765).

The exemplary promoters suitable for enhancing the rarD gene expression can be the potent promoters that are stronger than the native rarD promoter. For example, the lac promoter, the trp promoter, the trc promoter, the tac promoter, tet promoter, araBAD promoter, rpoH promoter, msrA promoter, Pm1 promoter (derived from the genus Bifidobacterium), and the PR and $P_L$ promoters of λ phage are all known to be potent promoters. Potent promoters providing a high level of gene expression in a bacterium belonging to the genus Pantoea can be used. Alternatively, the effect of a promoter can be enhanced by, for example, introducing a mutation into the promoter region of the rarD gene to obtain a stronger promoter function, thus resulting in the increased transcription level of the rarD gene located downstream of the promoter. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site greatly affects the translation efficiency of mRNA. For example, a 20-fold range in the expression levels was found, depending on the nature of the three nucleotides preceding the start codon (Gold L. et al., Annu. Rev. Microbiol., 1981, 35:365-403; Hui A. et al., EMBO J., 1984, 3:623-629).

The copy number, presence or absence of the rarD gene can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation and transformation of DNA, selection of an oligonucleotide as a primer, incorporation of mutations, and the like may be ordinary methods well-known to the persons skilled in the art. These methods are described, for example, in Sambrook J., Fritsch E. F. and Maniatis T., "Molecular Cloning: A Laboratory Manual", $2^{nd}$ ed., Cold Spring Harbor Laboratory Press (1989) or Green M. R. and Sambrook J. R., "Molecular Cloning: A Laboratory Manual", $4^{th}$ ed., Cold Spring Harbor Laboratory Press (2012); Bernard R. Glick, Jack J. Pasternak and Cheryl L. Patten, "Molecular Biotechnology: principles and applications of recombinant DNA", $4^{th}$ ed., Washington, D.C., ASM Press (2009).

Any methods for manipulation with recombinant DNA can be used including conventional methods such as, for example, transformation, transfection, infection, conjugation, and mobilization. Transformation, transfection, infection, conjugation or mobilization of a bacterium with the DNA encoding a protein can impart the bacterium the ability to synthesize the protein encoded by the DNA. Methods of transformation, transfection, infection, conjugation, and mobilization include any known methods. For example, a method of treating recipient cells with calcium chloride so as to increase permeability of the cells of E. coli K-12 to DNA has been reported for efficient DNA transformation and transfection (Mandel M. and Higa A., Calcium-dependent bacteriophage DNA infection, J. Mol. Biol., 1970, 53:159-162). Methods of specialized and/or generalized transduction were described (Morse M. L. et al., Transduction in Escherichia coli K-12, Genetics, 1956, 41(1):142-156; Miller J. H., Experiments in Molecular Genetics. Cold Spring Harbor, N.Y.: Cold Spring Harbor La. Press, 1972). Other methods for random and/or targeted integration of DNA into the host microorganism can be applied, for example, "lambda Red-recombineering" (Katashkina J. I. et al., Use of the λ Red-recombineering method for genetic engineering of Pantoea ananatis, BMC Mol. Biol., 2009, 10:34), "Mu-driven integration/amplification" (Akhverdyan et al., Appl. Microbiol. Biotechnol., 2011, 91:857-871), "Red/ET-driven integration" or "lambda Red/ET-mediated integration" (Datsenko K. A. and Wanner B. L., Proc. Natl. Acad. Sci. USA 2000, 97(12):6640-45; Zhang Y., et al., Nature Genet., 1998, 20:123-128). Moreover, for multiple insertions of desired genes in addition to Mu-driven replicative transposition (Akhverdyan et al., Appl. Microbiol. Biotechnol., 2011, 91:857-871) and chemically inducible chromosomal evolution based on recA-dependent homologous recombination resulted in an amplification of desired genes (Tyo K. E. J. et al., Nature Biotechnol., 2009, 27:760-765), another methods can be used, which utilize different combinations of transposition, site-specific and/or homologous Red/ET-mediated recombinations, and/or P1-mediated generalized transduction (see, for example, Minaeva N. I. et al., BMC Biotechnology, 2008, 8:63; Koma D. et al., Appl. Microbiol. Biotechnol., 2012, 93(2):815-829).

The phrase "native to" in reference to a protein or a nucleic acid native to a particular species of organisms such as, for example, mammals, plants, insects, bacteria, and viruses can refer to a protein or a nucleic acid that is native to that species. That is, a protein or a nucleic acid native to a particular species can mean the protein or the nucleic acid, respectively, that exists naturally in that species. A protein or a nucleic acid native to a particular species can be isolated from that species and sequenced using means known to the one of ordinary skill in the art. Moreover, as the amino acid sequence or the nucleotide sequence of a protein or nucleic acid, respectively, isolated from a species in which the protein or nucleic acid exists, can easy be determined, the phrase "native to" in reference to a protein or a nucleic acid can also refer to a protein or a nucleic acid that can be obtained using any means, for example, using a genetic engineering technique, including recombinant DNA technology, or a chemical synthesis method, or the like, so long as the amino acid sequence of the protein or the nucleotide sequence of the nucleic acid thus obtained is identical to the amino acid sequence of the protein or the nucleotide sequence of the nucleic acid that exists naturally in the species. The phrase "a protein" can include, but are not limited to, peptides, oligopeptides, polypeptides, proteins, enzymes, and so forth. The phrase "a nucleic acid" can include deoxyribonucleic acid (DNA) and ribonucleic acid (RNA), and can specifically include, but are not limited to, regulatory sequences, including promoters, attenuators, terminators, and the like, genes, intergenic sequences, sequences encoding signal peptides, pro-moieties of proteins, artificial amino acid sequences, and so forth.

The phrase "non-modified" in reference to a gene (for example, "a non-modified gene") or a protein (for example, "a non-modified protein") can mean a native gene or protein naturally expressed in or produced by an organism, specifically a non-modified bacterial strain belonging to the genus Pantoea such as, for example, by the P. ananatis 13355 strain. A non-modified protein can be encoded by a non-modified gene naturally occurring in genome of an organism, specifically a non-modified bacterial strain belonging to the genus Pantoea.

The metA gene of P. ananatis encodes a homoserine transsuccinylase MetA (EC 2.3.1.46). The amino acid sequence of the MetA protein native to P. ananatis is shown in SEQ ID NO: 10. The bacterium may have been modified further to include a metA gene encoding a MetA protein, wherein the arginine (Arg) residue at position 34 is replaced with cysteine (Cys) residue (R34C mutation) in the amino acid sequence of a wild-type MetA protein. The MetA protein having the R34C mutation is also referred to as "a mutant MetA protein". The metA gene encoding a mutant MetA protein is also referred to as "a mutant metA gene". The phrase "a wild-type MetA protein" can refer to a MetA protein not having the R34C mutation. A metA gene encoding a mutant MetA protein is also referred to as "a wild-type metA gene". Examples of the wild-type metA gene can include the metA gene native to P. ananatis and variants thereof provided that the variants do not have a mutation resulting in the R34C mutation of the encoded protein. Examples of the wild-type MetA protein can include the MetA protein native to *P. ananatis* and variants thereof provided that the variants do not have the R34C mutation. In other words, the mutant metA gene may be identical to any wild-type metA gene, except that the mutant metA gene has a mutation resulting in the R34C mutation of the encoded protein. Also, the mutant MetA protein may be identical to any wild-type MetA protein, except that the mutant MetA protein has the R34C mutation. Specifically, the amino acid sequence of the mutant MetA protein can be as shown in SEQ ID NO: 12, that is encoded by the mutant metA gene having the nucleotide sequence shown in SEQ ID NO: 11. That is, the mutant metA gene may have the nucleotide sequence of SEQ ID NO: 11, and the mutant MetA protein may have the amino acid sequence of SEQ ID NO: 12. The mutant metA gene may also have a variant nucleotide sequence of SEQ ID NO: 11, provided that the variant nucleotide sequence has a mutation resulting in the R34C mutation of the encoded protein. The mutant MetA protein may also have a variant amino acid sequence of SEQ ID NO: 12, provided that the variant amino acid sequence has the R34C mutation. The mutant MetA protein may be a homoserine transsuccinylase resistant to feedback inhibition by L-methionine. In other words, the MetA protein may be a protein having homoserine transsuccinylase activity and resistant to feedback inhibition by L-methionine. The aforementioned descriptions concerning variants of the rarD gene and the RarD protein can be similarly applied to variants of the metA gene and the MetA protein. The aforementioned descriptions concerning the phrase "the asparagine (Asn) residue at position 86 in the amino acid sequence of a wild-type RarD protein" can be applied similarly to the phrase "the arginine (Arg) residue at position 34 in the amino acid sequence of a wild-type MetA protein". The aforementioned descriptions concerning means for obtaining and introducing the mutant rarD gene can be applied similarly to means for obtaining and introducing the mutant metA gene.

The bacterium can have, in addition to the properties already mentioned, other specific properties such as various nutrient requirements, drug resistance, drug sensitivity, and drug dependence, without departing from the scope of the present invention.

2. Method

The method of producing L-methionine using a bacterium as described herein includes the steps of cultivating (also called culturing) the bacterium in a culture medium to allow L-methionine to be produced, excreted or secreted, and/or accumulated in the culture medium or in the bacterial cells, or both, and collecting the L-methionine from the culture medium and/or the bacterial cells. The method may include, optionally, the step of purifying L-methionine from the culture medium and/or the bacterial cells. L-methionine can be produced in such a form as described above. L-methionine can be produced particularly in a free form or as a salt thereof, or as a mixture of them. For example, sodium, potassium, ammonium, and the like salts or an inner salt such as zwitterion of L-methionine can be produced by the method. This is possible as amino acids can react under fermentation conditions with each other or a neutralizing agent such as an inorganic or organic acidic or alkaline substance in a typical acid-base neutralization reaction to form a salt that is the chemical feature of amino acids which is apparent to the person skilled in the art.

The cultivation of the bacterium, and collection and, optionally, purification of L-methionine from the medium and the like may be performed in a manner similar to the conventional fermentation methods wherein an L-amino acid or is produced using a microorganism. The culture medium can be either a synthetic or natural medium such as a typical medium that contains a carbon source, a nitrogen source, a sulphur source, a phosphorus source, inorganic ions, and other organic and inorganic components as required. As the carbon source, saccharides such as glucose, sucrose, lactose, galactose, fructose, arabinose, maltose, xylose, trehalose, ribose, and hydrolyzates of starches; alcohols such as ethanol, glycerol, mannitol, and sorbitol; organic acids such as gluconic acid, fumaric acid, citric acid, malic acid, and succinic acid; fatty acids, and the like can be used. As the nitrogen source, inorganic ammonium salts such as ammonium sulfate, ammonium chloride, and ammonium phosphate; organic nitrogen such as of soy bean hydrolysate; ammonia gas; aqueous ammonia; and the like can be used. Furthermore, peptone, yeast extract, meat extract, malt extract, corn steep liquor, and so forth can also be utilized. The medium may contain one or more types of these nitrogen sources. The sulphur source can include ammonium sulphate, magnesium sulphate, ferrous sulphate, manganese sulphate, and the like. The medium can contain a phosphorus source in addition to the carbon source, the nitrogen source and the sulphur source. As the phosphorus source, potassium dihydrogen phosphate, dipotassium hydrogen phosphate, phosphate polymers such as pyrophosphoric acid and so forth can be utilized. Vitamins such as vitamin B1, vitamin B2, vitamin B6, nicotinic acid, nicotinamide, vitamin B12, required substances, for example, organic nutrients such as nucleic acids such as adenine and RNA, amino acids, peptone, casamino acid, yeast extract, and the like may be present in appropriate, even if trace, amounts. Other than these, small amounts of calcium phosphate, iron ions, manganese ions, and so forth may be added, if necessary.

Cultivation can be performed under conditions suitable for cultivating a bacterium chosen for the use in the method for producing L-methionine. For example, the cultivation can be performed under aerobic conditions for from 16 to 72 hours or for from 16 to 24 hours, the culture temperature during cultivation can be controlled within from 30 to 45° C. or within from 30 to 37° C., and the pH can be adjusted between 5 and 8 or between 6 and 7.5. The pH can be adjusted using an inorganic or organic acidic or alkaline substance such as urea, calcium carbonate, or ammonia gas.

After cultivation, L-methionine can be collected from the culture medium. Also, after cultivation, L-methionine can be collected from the bacterial cells, specifically, the cells can be disrupted, a supernatant can be obtained by removing solids such as the cells and the cell-disrupted suspension (so-called cell debris), and then L-methionine can be collected from the supernatant. Disruption of the cells can be performed using, for example, methods that are well-known in the art, such as ultrasonic lysis using high frequency sound waves, or the like. Removal of solids can be performed by, for example, centrifugation or membrane filtration. Collection of L-methionine from the culture medium or the supernatant etc can be performed using, for example, conventional techniques such as concentration, crystallization, ion-exchange chromatography, medium or high pressure liquid chromatography, or a combination of these.

The collected L-methionine may contain bacterial cells, medium components, moisture, and by-product metabolites of the bacterium in addition to L-methionine. Purity of the collected L-methionine can be 50% or higher, 85% or higher, or 95% or higher (U.S. Pat. No. 5,431,933, Japanese Patent No. 1214636, U.S. Pat. Nos. 4,956,471, 4,777,051, 4,946,654, 5,840,358, 6,238,714, U.S. Patent Published Application No. 2005/0025878).

EXAMPLES

The present invention will be more precisely explained below with reference to the following non-limiting examples.

Example 1. Construction of L-Methionine-Producing Strain

It is known that biosynthesis of L-methionine can be affected positively by deleting the metJ gene encoding a negative transcription regulator of methionine regulon, and desensitizing the homoserine O-succinyltransferase (MetA) to the feedback inhibition by methionine and SAM (S-adenosyl methionine) (Chattopadhyay M. K. et al., Control of methionine biosynthesis in Escherichia coli K12: a closer study with analogue-resistant mutants, J. Gen. Microbiol., 1991, 137(3):685-691; Usuda Y. and Kurahashi O., Effects of deregulation of methionine biosynthesis on methionine excretion in Escherichia coli, Appl. Environ. Microbiol., 2005, 71(6):3228-3234). Therefore, metJ gene was deleted and a mutant metA gene was obtained in a P. ananatis bacterium.

1.1. Construction of P. ananatis SC17(0)ΔmetJ Strain

The P. ananatis SC17(0)ΔmetJ strain having deleted the metJ gene was constructed using λRed-dependent integration of the DNA fragment, that was obtained by PCR using the primers P1 (SEQ ID NO: 5) and P2 (SEQ ID NO: 6), and pMW118-attL-kan-attR plasmid as a template (Minaeva N. I. et al., BMC Biotechnol., 2008, 8:63), into P. ananatis SC17(0) strain (U.S. Pat. No. 8,383,372 B2, VKPM B-9246). The strain SC17(0) was deposited in the Russian National Collection of Industrial Microorganisms (VKPM; FGUP GosNII Genetika, Russian Federation, 117545 Moscow, 1st Dorozhny proezd, 1) on Sep. 21, 2005 under the accession number VKPM B-9246. The pMW118-attL-kan-attR plasmid (Japanese Patent Application Laid-Open Publication No. 2005-058227) was obtained by inserting attachment sites of the λ phage, attL and attR genes, and an antibiotic resistance gene (kan) into pMW118 (manufactured by Takara Bio Inc.) in the order of attL-kan-attR. The primers P3 (SEQ ID NO: 7) and P4 (SEQ ID NO: 8) were used to confirm the gene deletion. Thus, the P. ananatis SC17(0)ΔmetJ strain was constructed.

1.2. Selection of P. ananatis Strain Having a Mutant Allele of metA Gene Encoding Feedback Resistant MetA The cells of P. ananatis SC17(0)ΔmetJ strain were inoculated into 50 mL-flask containing L-broth (Sambrook J. and Russell D. W., Molecular Cloning: A Laboratory Manual (3rd ed.), Cold Spring Harbor Laboratory Press, 2001) up to $OD_{600}$ of 0.05 and cultured with aeration (250 rpm) at 34° C. for 2 hours. The exponentially growing cell culture of the strain at $OD_{600}$ of 0.25 was treated with NTG (final concentration 25 mg/L) for 20 minutes. The obtained culture was centrifuged, washed two times with fresh L-broth and spread onto M9-agarized plate containing glucose (0.2%) and norleucine (600 mg/L). Obtained mutant strains were tested for the ability to produce L-methionine. The strain having the highest ability to produce L-methionine was selected, and the nucleotide sequence of metA gene in that strain was determined. The sequence analysis revealed the mutation in the metA gene resulting in the replacement of the arginine (Arg) residue at position 34 with cysteine residue (R34C mutation) in the amino acid sequence of the wild-type MetA (SEQ ID NO: 10). The amino acid sequence of the mutant MetA protein having the R34C mutation is shown in SEQ ID NO: 12, and the nucleotide sequence of the mutant metA gene encoding the mutant MetA protein is shown in SEQ ID NO: 11. Thus, the P. ananatis SC17(0)ΔmetJ-metA(R34C) strain was constructed.

1.3. Overexpression of Wild-Type and Mutant rarD Gene in P. ananatis Strain

The rarD gene was overexpressed by placing it under the control of a constitutive promoter of the nlpD gene native to Escherichia coli. Firstly, a vector containing the promoter was constructed. A DNA fragment was obtained by PCR using the primers P5 (SEQ ID NO: 13) and P6 (SEQ ID NO: 14), and chromosomal DNA of E. coli strain MG1655 (ATCC No. 47076) as a template. The resulting DNA fragment was purified using an agarose gel electrophoresis and then isolated (Qiaquick Gel Extraction Kit, Qiagen). The DNA fragment was treated with the restriction enzymes PaeI and SalI (Fermentas) and cloned into the vector pMIV-5JS (RU2458981 C2) cleaved with PaeI/SalI. Thus, the pMIV-Pnlp vector was constructed.

Then, rarD gene was obtained by PCT using the primers P7 (SEQ ID NO: 15) and P8 (SEQ ID NO: 16), and chromosomal DNA of the P. ananatis SC17 strain (FERM BP-11091) as a template. The SC17 strain was deposited at the independent administrative agency, National Institute of Advanced Industrial Science and Technology, International Patent Organism Depositary (currently, independent administrative agency, National Institute of Technology and Evaluation, International Patent Organism Depositary (NITE IPOD), #120, 2-5-8 Kazusakamatari, Kisarazu-shi, Chiba, 292-0818, Japan) on Feb. 4, 2009, and assigned an accession number of FERM BP-11091. The resulting DNA fragment was purified and isolated as described above, treated with the restriction enzymes SalI and XbaI (Fermentas) and cloned into the vector pMIV-Pnlp cleaved with SalI/XbaI. Thus, the pMIV-Pnlp-rarD plasmid harboring the wild-type rarD gene was obtained. We found that the plasmid pMIV-Pnlp-rarD can confer on the P. ananatis SC17 strain a resistance to 0.5 g/L of alpha-methyl-DL-methionine (Chattopadhyay M. K. et al., Control of methionine biosynthesis in Escherichia coli K12: a closer study with analogue-resistant mutants, J. Gen. Microbiol., 1991, 137(3):685-691).

The P. ananatis SC17 strain was transformed with the plasmid pMIV-Pnlp-rarD, and the strain resistant to 1 g/L of alpha-methyl-DL-methionine and 0.8 g/L of nor-leucine was selected. Analysis of the nucleotide sequence of rarD gene revealed the substitution of the "aac" codon encoding the asparagine (Asn, N) residue to the "gac" codon encoding the aspartic acid (Asp, D) residue at the positions from 256 to 258 in the nucleotide sequence of the wild-type rarD gene (SEQ ID NO: 1). This substitution in the nucleotide sequence of the wild-type rarD gene resulted in the replacement of the asparagine residue at position 86 with aspartic acid residue (N86D mutation) in the amino acid sequence of the wild-type RarD protein (SEQ ID NO: 2). The pMIV-Pnlp-rarD(N86D) plasmid harboring the mutant rarD gene (SEQ ID NO: 3) that encodes the mutant RarD protein (SEQ ID NO: 4) was isolated from the strain.

The pMIV-Pnlp-rarD and pMIV-Pnlp-rarD(N86D) plasmids were introduced into SC17(0)ΔmetJ-metA(R34C) strain (Example 1.2) using a routine electroporation procedure. Thus, the P. ananatis SC17(0)ΔmetJ-metA(R34C)/ pMIV-Pnlp-rarD and SC17(0)ΔmetJ-metA(R34C)/pMIV-Pnlp-rarD(N86D) strains were constructed. As a control, the P. ananatis SC17(0)ΔmetJ-metA(R34C)/pMIV-5JS strain was obtained.

Example 2. Production of L-Methionine

The P. ananatis SC17(0)ΔmetJ-metA(R34C)/pMIV-5JS, SC17(0)ΔmetJ-metA(R34C)/pMIV-Pnlp-rarD, and SC17(0)ΔmetJ-metA(R34C)/pMIV-Pnlp-rarD(N86D) strains were each cultivated at 32° C. for 18 hours in LB-medium (also referred to as lysogenic broth or Luria-Bertani medium as described in Sambrook, J. and Russell, D. W. "Molecular Cloning: A Laboratory Manual", 3rd ed., Cold Spring Harbor Laboratory Press (2001)). Then, 0.2 mL of the obtained cultures were inoculated into 2 mL of a fermentation medium in 20×200-mm test tubes and cultivated at 32° C. for 48 hours on a rotary shaker at 250 rpm until glucose was consumed.

The composition of the fermentation medium (g/L) was as follows:

| | |
|---|---|
| Glucose | 40.0 |
| $(NH_4)_2SO_4$ | 15.0 |
| $KH_2PO_4$ | 1.5 |
| $MgSO_4 \times 7H_2O$ | 1.0 |
| Thiamine-HCl | 0.1 |
| $CaCO_3$ | 25.0 |
| LB-medium | 4% (v/v) |

The fermentation medium was sterilized at 116° C. for 30 min, except that glucose and $CaCO_3$ were sterilized separately as follows: glucose at 110° C. for 30 min and $CaCO_3$ at 116° C. for 30 min. The pH was adjusted to 7.0 by KOH solution.

After cultivation, the amount of accumulated L-methionine was determined using Agilent 1260 amino-acid analyzer. The results of six independent test tube fermentations (as average values±standard deviations) are shown in Table 1. As one can see from the Table 1, the modified P. ananatis SC17(0)ΔmetJ-metA(R34C)/pMIV-Pnlp-rarD strain was able to produce a higher amount (g/L) of L-methionine (Met) as compared with the parental P. ananatis SC17(0)ΔmetJ-metA(R34C)/pMIV-5JS strain. Moreover, the Table 1 also shows that the modified P. ananatis SC17(0)ΔmetJ-metA(R34C)/pMIV-Pnlp-rarD(N86D) strain having the mutant rarD gene that encodes the mutant RarD protein was able to produce a higher amount of Met as compared with the P. ananatis SC17(0)ΔmetJ-metA(R34C)/pMIV-Pnlp-rarD strain.

TABLE 1

| P. ananatis strain | Met, g/L |
|---|---|
| SC17(0)ΔmetJ-metA(R34C)/pMIV-5JS (control strain) | 0.34 ± 0.01 |
| SC17(0)ΔmetJ-metA(R34C)/pMIV-Pnlp-rarD | 0.81 ± 0.02 |
| SC17(0)ΔmetJ-metA(R34C)/pMIV-Pnlp-rarD(N86D) | 1.33 ± 0.02 |

While the invention has been described in detail with reference to preferred embodiments thereof, it will be apparent to the one of ordinary skill in the art that various changes can be made, and equivalents employed, without departing from the scope.

INDUSTRIAL APPLICABILITY

The method of the present invention is useful for the production of L-methionine by fermentation of a bacterium.

The invention claimed is:

1. A method for producing L-methionine or a salt thereof comprising:
   (i) cultivating in a culture medium a bacterium of the genus *Pantoea* to produce and accumulate the L-methionine or a salt thereof in the culture medium and/or the bacterium, and
   (ii) collecting the L-methionine or the salt thereof from the culture medium and/or the bacterium,
   wherein said bacterium has been modified to overexpress a gene encoding a transporter protein compared to the expression of said gene encoding a transporter protein in the corresponding non-modified *Pantoea* bacterium,
   wherein said gene encoding a transporter protein is selected from the group consisting of:
   (A) a DNA comprising the nucleotide sequence of SEQ ID NO: 1,
   (B) a DNA encoding a protein comprising the amino acid sequence of SEQ ID NO: 2,
   (C) a DNA encoding a protein that comprises all of SEQ ID NO: 2 except for substitution, deletion, insertion, and/or addition of 1 to 30 amino acids in SEQ ID NO: 2, and
   (D) a DNA encoding a protein having a sequence identity of not less than 90% to the entire amino acid sequence of SEQ ID NO: 2, and
   wherein said gene encoding a transporter protein is overexpressed as compared with the corresponding non-modified *Pantoea* bacterium by increasing the copy number of the gene encoding a transporter protein and/or by modifying an expression regulatory region of the gene encoding a transporter protein, so that the expression of said gene is enhanced as compared with the corresponding non-modified *Pantoea* bacterium.

2. The method according to claim 1, wherein said transporter protein has an amino acid substitution, wherein the amino acid at the position corresponding to position 86 of the amino acid sequence of SEQ ID NO: 2 is replaced with an acidic amino acid residue.

3. The method according to claim 2, wherein said acidic amino acid residue is an aspartic acid residue or a glutamic acid residue.

4. The method according to claim 1, wherein said bacterium has been modified further to comprise a gene encoding a homoserine transsuccinylase protein, wherein said gene encoding the homoserine transsuccinylase protein is selected from the group consisting of:
   (A) a DNA comprising the nucleotide sequence of SEQ ID NO: 11,
   (B) a DNA encoding a protein comprising the amino acid sequence of SEQ ID NO:12,
   (C) a DNA encoding a protein that comprises all of SEQ ID NO: 12 except for substitution, deletion, insertion, and/or addition of 1 to 30 amino acids in SEQ ID NO: 12, and wherein said protein comprises a cysteine at the position corresponding to position 34 of the polypeptide of SEQ ID NO: 10 and
   (D) a DNA encoding a protein having a sequence identity of not less than 90% to the entire amino acid sequence of SEQ ID NO: 12, and wherein said protein comprises a cysteine at the position corresponding to position 34 of the polypeptide of SEQ ID NO: 10.

5. The method according to claim 1, wherein said bacterium is *Pantoea ananatis*.

6. The method according to claim 1, wherein said gene encoding the transporter protein is selected from the group consisting of:
   (A) a DNA comprising the nucleotide sequence of SEQ ID NO: 1,
   (B) a DNA encoding a protein comprising the amino acid sequence of SEQ ID NO: 2,
   (C) a DNA encoding a protein that comprises all of SEQ ID NO: 2 except for substitution, deletion, insertion, and/or addition of 1 to 10 amino acids in SEQ ID NO: 2, and
   (D) a DNA encoding a protein having a sequence identity of not less than 96% to the entire amino acid sequence of SEQ ID NO: 2.

7. The method according to claim 1, wherein said gene encoding the transporter protein is selected from the group consisting of:
   (A) a DNA comprising the nucleotide sequence of SEQ ID NO: 1,
   (B) a DNA encoding a protein comprising the amino acid sequence of SEQ ID NO: 2,
   (C) a DNA encoding a protein that comprises all of SEQ ID NO: 2 except for substitution, deletion, insertion, and/or addition of 1 to 5 amino acids in SEQ ID NO: 2, and
   (D) a DNA encoding a protein having a sequence identity of not less than 98% to the entire amino acid sequence of SEQ ID NO: 2.

\* \* \* \* \*